(12) United States Patent
Estevanell

(10) Patent No.: US 10,413,452 B2
(45) Date of Patent: Sep. 17, 2019

(54) CLOTH-SILICONE NURSING PAD ASSEMBLY

(71) Applicant: Ramon Estevanell, Brooklyn, NY (US)

(72) Inventor: Ramon Estevanell, Brooklyn, NY (US)

( * ) Notice: Subject to any disclaimer, the term of this patent is extended or adjusted under 35 U.S.C. 154(b) by 51 days.

(21) Appl. No.: 15/669,930

(22) Filed: Aug. 6, 2017

(65) Prior Publication Data
US 2019/0038475 A1    Feb. 7, 2019

(51) Int. Cl.
*A61F 13/14* (2006.01)
*A61L 15/22* (2006.01)
*A61L 15/58* (2006.01)
*A61L 15/52* (2006.01)
*A61L 15/40* (2006.01)
*B32B 7/12* (2006.01)
*B32B 5/02* (2006.01)
*B32B 3/26* (2006.01)
*B32B 27/08* (2006.01)
*B32B 27/12* (2006.01)

(52) U.S. Cl.
CPC .......... *A61F 13/141* (2013.01); *A61L 15/225* (2013.01); *A61L 15/40* (2013.01); *A61L 15/52* (2013.01); *A61L 15/58* (2013.01); *B32B 3/266* (2013.01); *B32B 5/024* (2013.01); *B32B 7/12* (2013.01); *B32B 27/08* (2013.01); *B32B 27/12* (2013.01); *B32B 2307/726* (2013.01); *B32B 2307/728* (2013.01); *B32B 2555/00* (2013.01)

(58) Field of Classification Search
CPC .................. A61F 13/141; A61F 2013/15016
See application file for complete search history.

(56) References Cited

U.S. PATENT DOCUMENTS

| | | | | |
|---|---|---|---|---|
| 4,125,114 A | * | 11/1978 | Repke | A61F 13/141 604/366 |
| 5,732,714 A | * | 3/1998 | Morrissey | A61J 13/00 128/846 |
| 7,905,763 B1 | * | 3/2011 | Frank | A61F 13/141 450/37 |
| 2003/0073930 A1 | * | 4/2003 | Morrissey | A61J 13/00 600/573 |
| 2004/0153041 A1 | * | 8/2004 | Giloh | A61F 13/15804 604/358 |
| 2006/0089082 A1 | * | 4/2006 | Pawloski | A61F 13/141 450/37 |
| 2009/0298386 A1 | * | 12/2009 | Deal | A41C 3/065 450/81 |
| 2009/0308405 A1 | * | 12/2009 | Yamashita | A61J 13/00 128/890 |
| 2012/0080437 A1 | * | 4/2012 | Guenther | A61M 1/14 220/501 |

* cited by examiner

Primary Examiner — Ariana Zimbouski

(57) ABSTRACT

A nursing pad assembly is described, combining adherence and water resistant advantages of silicone lamina with the comfort and absorption of an attached cloth layer. In particular, a nipple contact area passes through an aperture in the silicone lamina. In one embodiment the cloth layer includes at least three sub-layers engineered for toweling, wicking/absorption, and water resistant properties, respectively.

19 Claims, 6 Drawing Sheets

CLOTH-SILICONE NURSING PAD ASSEMBLY

FIELD OF THE INVENTION

The field of the present invention generally relates to post-partum maternity needs, and in particular nursing accessories.

BACKGROUND OF THE INVENTION

Breastfeeding mothers commonly experience milk leakage, often soiling outer garments. Three main solutions are on the market today. Disposable Nursing Pads, Cloth Nursing Pads, and Silicone Nursing Pads. These each have their advantages and disadvantages, all of which the present invention sets out to address holistically.

The first solution, disposable nursing pads, present the same environmental costs as diapers do (utilizing raw materials and filling landfills), which are increasingly important to earth-conscious consumers. These disposable nursing pads feature a peel-and-stick area to help secure the pad inside a shirt or bra. On some fabrics and garments it is difficult to secure these pads. Further still, because they do not adhere to the skin, they can shift with clothing and slip off of the nipple, allowing leaking to occur.

The second solution, cloth nursing pads, is designed to be washable and reusable. Featuring a soft fabric in one or more layers, these pads can absorb a reasonable quantity of milk; however, as they do not adhere to the skin, they may not remain securely in place over the nipple, eventually allowing some leakage. Furthermore, once the cloth nursing pad has absorbed milk, even gentle pressure to the absorbent material can cause some milk can run down the breast.

The third solution, silicone nursing pads, is also washable and reusable. A silicone lamina, has the general advantage of tightly adhering to the skin, making a seal around the nipple. With silicone nursing pads, there is no capacity to absorb the milk, and as some milk expresses and escapes to the area between the breast and the silicone nursing pad, it can build enough pressure to cause the milk to leak and quickly soil garments.

SUMMARY OF THE INVENTION

The three existing solutions have their drawbacks, all of which the present invention aims to overcome. By combining the hydrophobic adherence of a silicone lamina with the absorbency of a composite cloth layer, wicking milk away from the silicone seal, the present invention elegantly overcomes the prior setbacks.

In one preferred embodiment of the invention, the nursing pad assembles a silicone lamina with a cloth layer, by securely buttoning a nipple contact area through an aperture in the silicone lamina. This nipple contact area serves the functional purpose of securing the two layers (both silicone and cloth), as well as being the nipple's contact point where the process of capillary action absorbs milk into the cloth. In a further embodiment, the aperture can be ¾" in diameter. In another embodiment the lamina can be a silicone, thermoplastic elastomer (TPE), ethylene-vinyl-acetate (EVA), acrylic, natural rubber, synthetic rubber, any elastomer material or pressure sensitive adhesive. In a further embodiment, the lamina can be a medical grade adhesive which is inert and safe for neonatal and infant contact and ingestion.

In a further embodiment of the invention, the nursing pad assembles a silicone lamina with an absorbing composite cloth layer formed of at least three cloth sub-layers. Each of the cloth sub-layers is engineered for different purpose, and accordingly can be made of different sizes and materials.

The first cloth sub-layer (the nipple contact area) is an inner small toweling layer for comfort and absorption. This first cloth sub-layer can be larger in diameter than the aperture on the silicone lamina. In a further embodiment, this first cloth sub-layer can be ¼" larger in diameter or 25% larger in diameter than the aperture on the silicone lamina. In a further embodiment, this first cloth sub-layer can be 1" in diameter and the aperture on the silicone lamina can be ¾" in diameter. In a further embodiment, the first cloth sub-layer can be cotton, velvet, velour, micro chamois, French terry, bamboo, hemp, flannel or fleece.

The second cloth sub-layer (the wicking/absorbing area, an absorbent reservoir) would be a middle layer which functions to absorb the breast milk coming from the first sub-layer and then to wick it throughout the second cloth sub-layer's expanse. In a further embodiment, this second cloth sub-layer can be ¼" larger in diameter than the silicone lamina's overall size. In a further embodiment the second cloth sub-layer can be made from microfiber terry soaker fabric, tangled cellulose fiber fabric (such as Zorb™) cotton, hemp fabric or bamboo fabric. In a further embodiment the second cloth sub-layer can be made from one or more individual sub-sub-layers of each made from one or more materials. In a further embodiment the second cloth sub-layer can have one or more intervening layers separating it from the first cloth sub-layer and/or third cloth sub-layer.

The third cloth sub-layer (the water resistant/waterproof surface) would serve as the outer layer with water resistance/waterproof capabilities for containment, so that the breast milk does not leak onto outer garments. In one embodiment, this third cloth sub-layer can be of the same size as the second layer. In one embodiment, this third cloth sub-layer can be made of polyurethane laminate (PUL), thermoplastic polyurethane (TPU), neoprene, wool, fleece, nylon, polyester or synthetic water resistant fabric.

Together, these three cloth sub-layers (inner, middle, and outer) would be assembled co-axially and attached at their centers either with stitching or adhesive.

In one embodiment, the silicone lamina is formed of a curved shape with a 1" apex height, measuring 3" in diameter with a ¾" aperture at its center. In this embodiment, the concave (inner) side is molded with a smooth surface texture providing sufficient adhesion for secure attachment to the breast. In one embodiment, the convex (outer) side is form of a less-adhesive surface texture.

BRIEF DESCRIPTION OF THE DRAWINGS

Preferred and alternative examples of the present invention are described in detail below with reference to the following Figure drawings.

DETAILED DESCRIPTION

Figure 1:
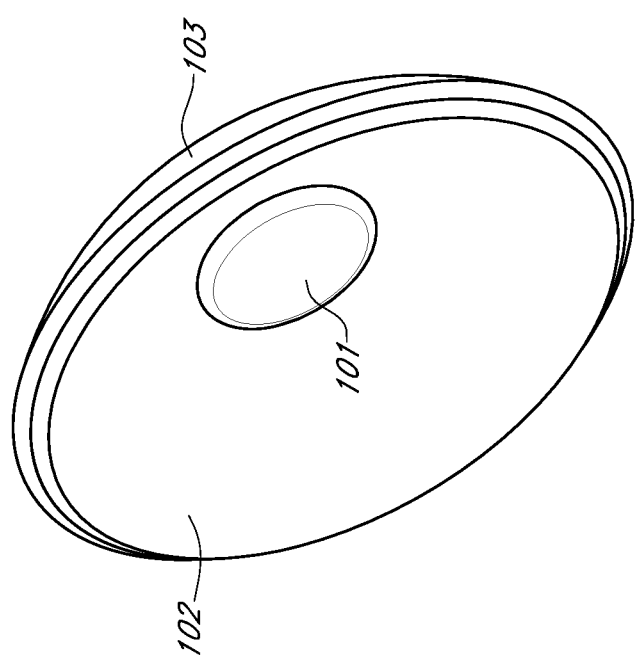
FIG. 1 is a perspective rendering of an assembled nursing pad that shows the silicone lamina layer together with the cloth layer from a concave perspective.

The invention shown in FIG. 1 is an assembled nursing pad, featuring a first 102 breast-shaped lamina made of silicone (or any other washable, flexible, self-adhering, waterproof material) on the concave interior surface of the assembled nursing pad, having an aperture in the silicone lamina. The nursing pad assembly shown in FIG. 1 further comprises a second, 103 cloth lamina adjacent to the convex side of the first lamina and having 101 a nipple contact area protruding through the aperture in the silicone layer, which contact area is larger in diameter than the aperture, allowing the cloth lamina to securely assemble and also make contact with the nipple.

Figure 2:
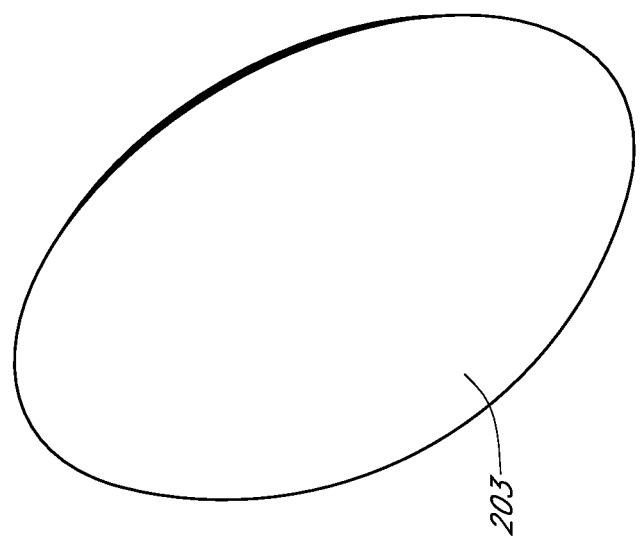
FIG. 2 is a perspective rendering of an assembled nursing pad that shows the cloth layer from a convex perspective.

The invention shown in FIG. 2 is an assembled nursing pad, as in FIG. 1, but showing the convex view with only the 203 cloth lamina visible.

Figure 3:
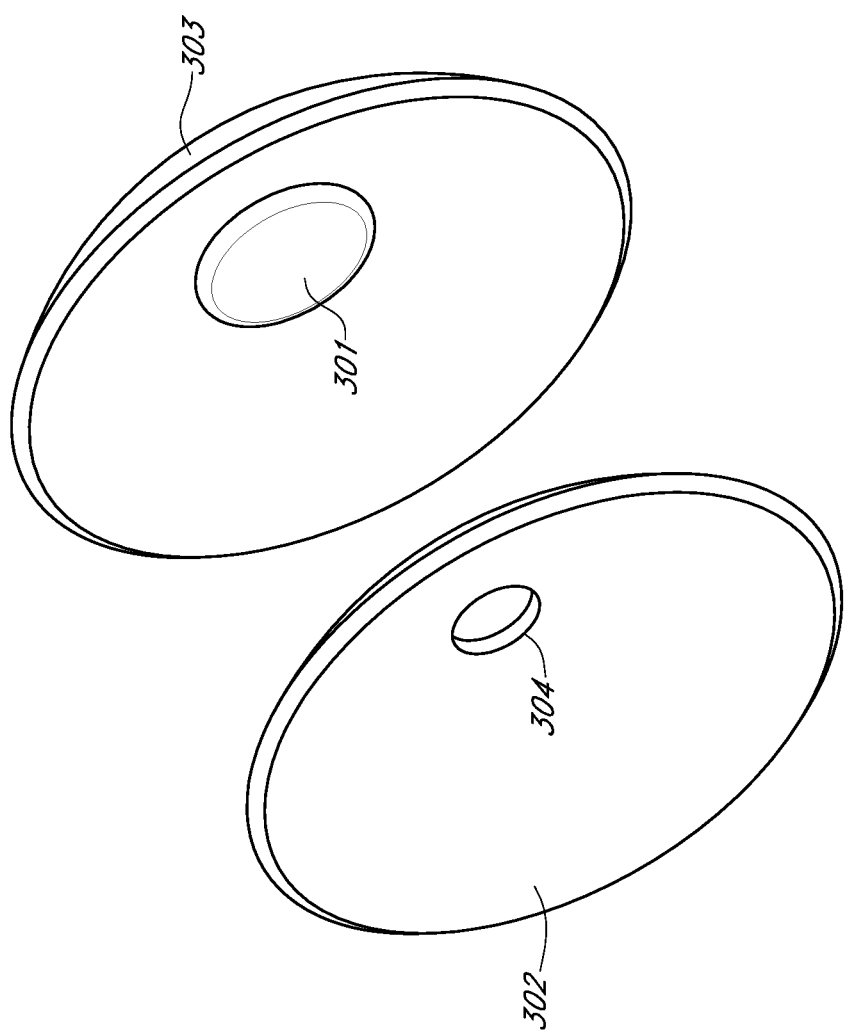
FIG. 3 is a perspective rendering of a nursing pad that shows the silicone lamina layer separated from the cloth layer.

The invention shown in FIG. 3 is a disassembled nursing pad, separately showing the 302 silicone lamina with its 304 aperture and 303 cloth layers with a 301 nipple contact area.

Figure 5:
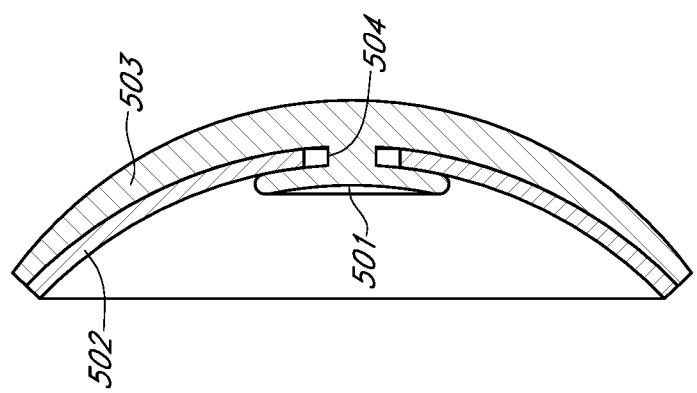
FIG. 5 is a cross-sectional side-view looking at the assembled nursing pad from the cross section shown in FIG. 4.
Figure 4:
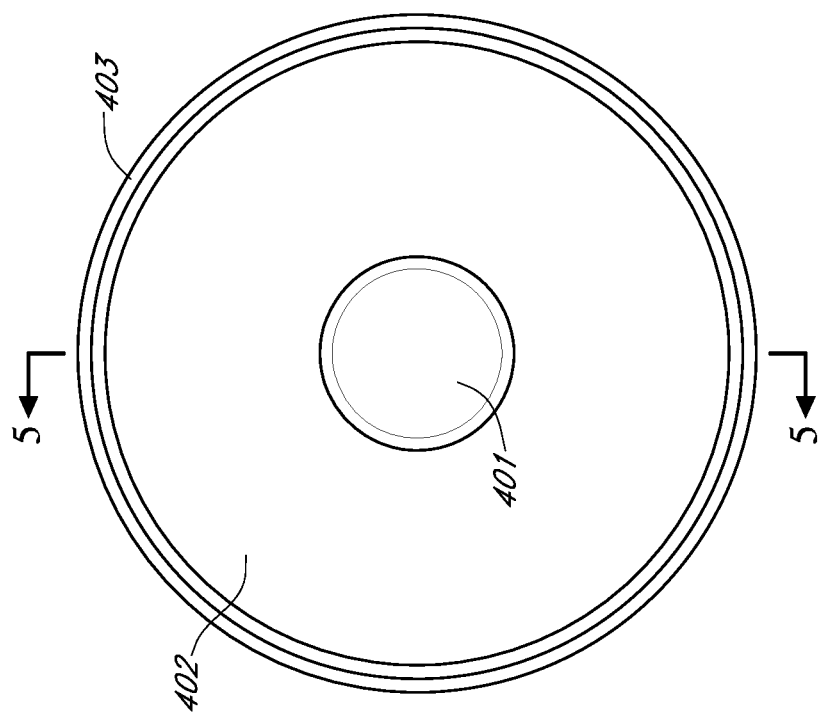
FIG. 4 is a concave end view of an assembled nursing pad that shows the cloth layer protruding inward through the silicone lamina layer.

The invention shown in FIG. 4 (concave end-view) and FIG. 5 (cross-sectional side-view) is an assembled nursing pad, featuring 402, 502 silicone lamina, 403, 503 cloth layer, and 401, 501 nipple contact area protruding inward through the 504 aperture in the 402, 502 silicone lamina. The 401, 501 nipple contact area has a larger diameter than the 504 aperture in the 402, 502 silicone lamina to allow the cloth layer and silicone lamina to assemble securely. In one embodiment the aperture is ¾" in diameter and the nipple contact area is 1" in diameter.

Figure 7:
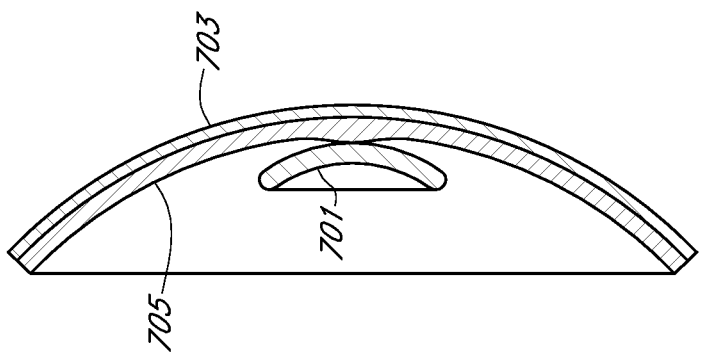
FIG. 7 is a cross-sectional side-view showing the three cloth sub-layers of FIG. 6 as assembled.
Figure 6:
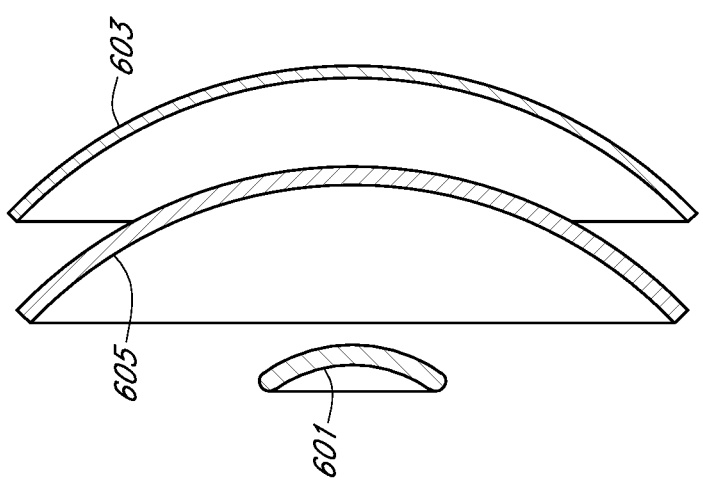
FIG. 6 is a cross-sectional side-view showing three cloth sub-layers separated.

The further embodiment of the invention shown in FIG. 6 and FIG. 7 shows a composite cloth comprising three cloth sub-layers: 601, 701 a nipple contact cloth sub-layer, 605, 705 a wicking/absorbing cloth sub-layer, and 603, 703 a water resistant/waterproof cloth sub-layer. In particular, FIG. 6 shows the three cloth sub-layers separately (unassembled) and FIG. 7 shows the three cloth sub-layers as assembled.

Figure 9:
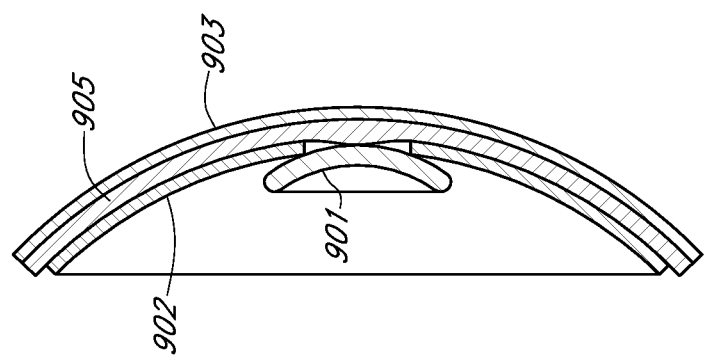
FIG. 9 is a cross-sectional side-view looking at the assembled nursing pad featuring three cloth sub-layers from the cross section shown in FIG. 8.
Figure 8:
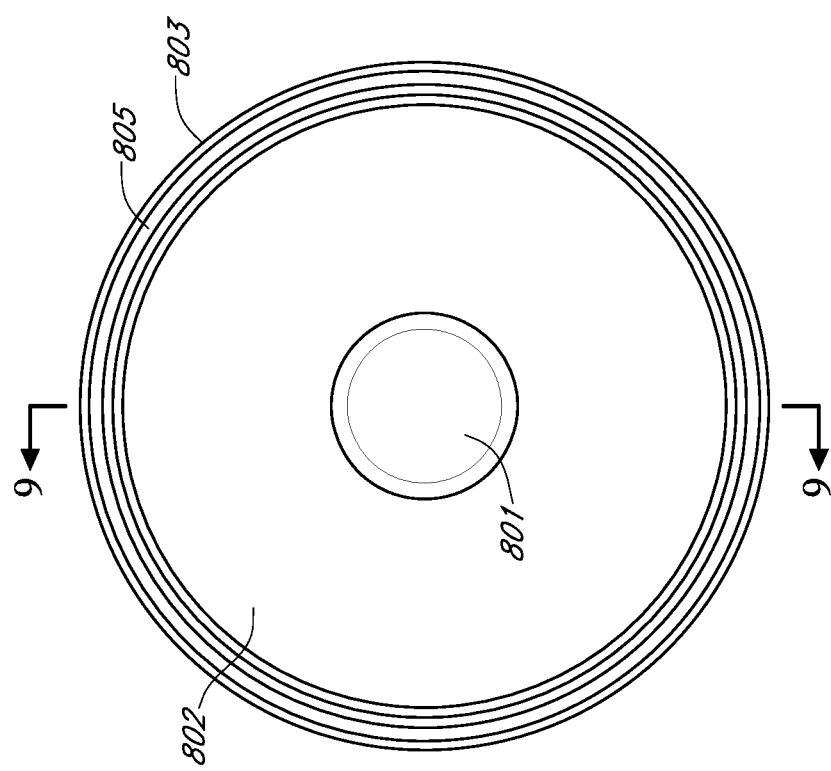
FIG. 8 is a concave end view of an assembled nursing pad featuring three cloth sub-layers (toweling, absorbent/wicking, waterproof surface)

The further embodiment of the invention shown in FIG. 8 (concave end-view) and FIG. 9 (cross-sectional side-view) is an assembled nursing pad with performance engineered cloth tri-layer construction. The 802, 902 silicone lamina is assembled securely to the 801, 805, 803, 901, 905, 903 composite tri-layer cloth. The 801, 901 nipple contact area is a comfortable absorbing toweling sub-layer functioning to wick milk through the aperture towards the middle layer via capillary action. The 805, 905 middle layer is an absorbent wicking layer. The 803, 903 outer layer is a water resistant/waterproof surface layer, to protect outer garments from leaking.

Figure 10:
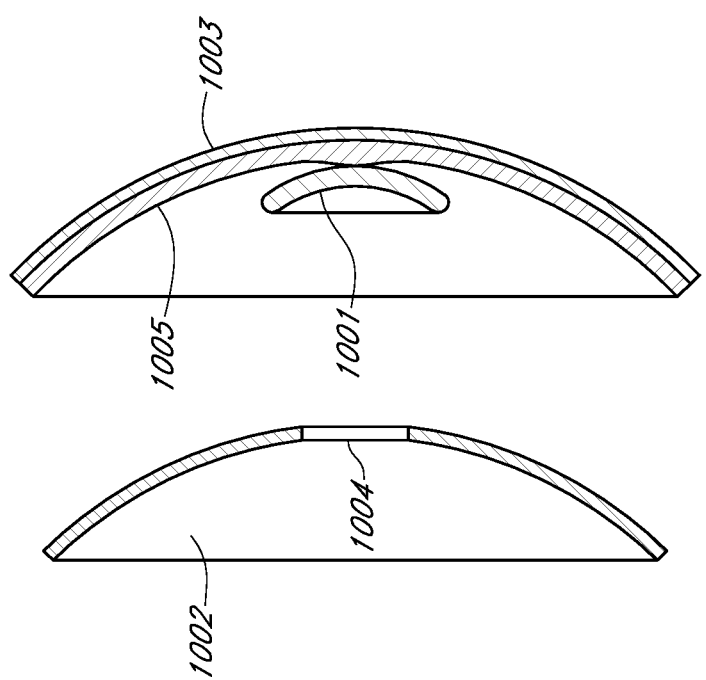
FIG. 10 is a cross-sectional side-view as in FIG. 9, but here showing the silicone lamina layer separated (disassembled) from the three composite cloth sub-layers.

The further embodiment of the invention shown in FIG. 10 is a disassembled nursing pad, separately showing 1002 the silicone lamina and 1001, 1005, 1003 composite cloth sub-layers. The 1002 silicone lamina features 1004 an aperture at its center. In one embodiment the 1004 aperture can be ¾" in diameter. The composite cloth comprises three sub-layers: 1001 a nipple contact cloth sub-layer, 1005 a middle absorbent wicking layer, and 1003 a water resistant/waterproof surface layer.

The invention claimed is:

1. An apparatus, comprising:
an inner layer and an outer layer;
wherein the inner layer has an aperture centered therein, an aperture diameter, an interior side and an exterior side;
wherein the inner layer is water resistant;
wherein the interior side of the inner layer adheres removably to a breast by means of a pressure sensitive adhesive;
wherein the outer layer is securely attachable to the inner layer;
wherein the outer layer comprises an absorbent reservoir;
wherein the outer layer is comprised of at least three sub-layers;
wherein the at least three sub-layers comprise: a nipple contact layer, an absorbent reservoir and a water resistant outer layer;
wherein the nipple contact layer comprises an absorbent material;
wherein the absorbent reservoir comprises an absorbent material;
wherein the water resistant outer layer comprises a water resistant material.

2. The apparatus of claim 1 wherein the outer layer comprises a button-shaped protrusion having a base diameter and an outer diameter, and securable to the inner layer by inserting the button-shaped protrusion from the exterior side of the inner layer through the aperture of the inner layer to the interior side of the inner layer;
wherein the outer diameter of the button-shaped protrusion is larger than the aperture diameter of the inner layer.

3. The apparatus of claim 2 wherein the button-shaped protrusion comprises the nipple contact layer.

4. The apparatus of claim 1 wherein the nipple contact layer functions to absorb expressed breast milk and transfer it to the absorbent reservoir via capillary action.

5. The apparatus of claim 1 wherein the absorbent reservoir is positioned adjacent to the exterior side of the inner layer.

6. The apparatus of claim 1 wherein at least 60% by volume of the absorbent reservoir is positioned adjacent to the exterior side of the inner layer.

7. The apparatus of claim 1 wherein at least 80% by volume of the absorbent reservoir is positioned adjacent to the exterior side of the inner layer.

8. The apparatus of claim 5 wherein expressed breast milk absorbed by the nipple contact layer transfers via capillary action from the nipple contact layer into the absorbent reservoir.

9. The apparatus of claim 8 wherein expressed breast milk absorbed by the absorbent reservoir is dispersed throughout the absorbent reservoir via capillary action.

10. The apparatus of claim 1 wherein the inner layer is selected from the group consisting of: silicone, thermoplastic elastomers, ethylene-vinyl-acetate, acrylic, natural rubber and synthetic rubber.

11. The apparatus of claim 1 wherein the inner layer is silicone.

12. The apparatus of claim 1 wherein the nipple contact layer is selected from the group consisting of: cotton, velvet, velour, micro chamois, French terry, bamboo, hemp flannel and fleece.

13. The apparatus of claim 1 wherein the nipple contact layer is velour.

14. The apparatus of claim 1 wherein the absorbent reservoir is selected from the group consisting of: microfiber terry soaker fabric, tangled cellulose fiber fabric, cotton, hemp fabric and bamboo fabric.

15. The apparatus of claim 1 wherein the absorbent reservoir is tangled cellulose fiber fabric.

16. The apparatus of claim 1 wherein the water resistant outer layer is selected from the group consisting of: polyurethane laminate, thermoplastic polyurethane, neoprene, wool, fleece, nylon, polyester and synthetic water resistant fabric.

17. The apparatus of claim 1 wherein the water resistant outer layer is polyester.

18. The apparatus of claim 3 wherein the inner layer is silicone, the nipple contact layer is velour, the absorbent reservoir is tangled cellulose fiber fabric, and the water resistant outer layer is polyester.

19. The apparatus of claim 9 wherein the inner layer is silicone, the nipple contact layer is velour, the absorbent reservoir is tangled cellulose fiber fabric, and the water resistant outer layer is polyester.

* * * * *